US012630494B2

(12) United States Patent
Matsumoto et al.

(10) Patent No.: US 12,630,494 B2
(45) Date of Patent: May 19, 2026

(54) ACETIC ACID MANUFACTURING METHOD

(71) Applicant: KELLOGG BROWN & ROOT LLC, Houston, TX (US)

(72) Inventors: Tadashi Matsumoto, Yokohama (JP); Toshihide Hirai, Yokohama (JP); Yui Kotani, Yokohama (JP); Daisuke Honda, Yokohama (JP)

(73) Assignee: Kellogg Brown & Root LLC, Houston, TX (US)

( * ) Notice: Subject to any disclaimer, the term of this patent is extended or adjusted under 35 U.S.C. 154(b) by 994 days.

(21) Appl. No.: 17/640,522

(22) PCT Filed: Sep. 3, 2020

(86) PCT No.: PCT/JP2020/033411
§ 371 (c)(1),
(2) Date: Mar. 4, 2022

(87) PCT Pub. No.: WO2021/045145
PCT Pub. Date: Mar. 11, 2021

(65) Prior Publication Data
US 2022/0324787 A1      Oct. 13, 2022

(30) Foreign Application Priority Data

Sep. 5, 2019    (JP) ................................. 2019-161901

(51) Int. Cl.
*C07C 51/44*          (2006.01)
*C07C 51/12*          (2006.01)
(52) U.S. Cl.
CPC .............. *C07C 51/44* (2013.01); *C07C 51/12* (2013.01)
(58) Field of Classification Search
CPC .......... C07C 51/44; C07C 51/12; C07C 53/08
See application file for complete search history.

(56) References Cited

U.S. PATENT DOCUMENTS 10,308,581 B2    6/2019    Shimizu
2013/0261334 A1    10/2013    Shimizu et al.
(Continued)

FOREIGN PATENT DOCUMENTS

EP          2653460 B1      10/2013
EP          3219699 B1      9/2017
(Continued)

OTHER PUBLICATIONS

International Search Report dated Oct. 27, 2020, issued in counterpart International Application No. PCT/JP2020/033411 (3 pages).
(Continued)

*Primary Examiner* — Jafar F Parsa
(74) *Attorney, Agent, or Firm* — Gary M. Machetta

(57)          ABSTRACT

Acetic acid is manufactured by a method of carbonylating raw material with carbon monoxide, the method comprising: a reaction step of forming a reaction mixture containing acetic acid inside a reactor; and a purification step of purifying the reaction mixture to thereby obtain product acetic acid. The purification step includes: a flash evaporation step of separating the reaction mixture into a vapor-phase mixture and a liquid-phase mixture; a first distillation step of distilling the vapor-phase mixture to thereby separate and remove low-boiling point components and obtain crude acetic acid; and a second distillation step of introducing the crude acetic acid into a heavy ends column and distilling the crude acetic acid to thereby purify the crude acetic acid and obtain product acetic acid. In the second distillation step, the low-boiling point components remaining in the crude acetic acid are drawn out from a column top of the heavy ends column.

10 Claims, 5 Drawing Sheets

(56)            References Cited

U.S. PATENT DOCUMENTS

| | | |
|---|---|---|
| 2017/0349521 A1 | 12/2017 | Shimizu et al. |
| 2019/0292124 A1 | 9/2019 | Hallinan et al. |
| 2020/0172461 A1* | 6/2020 | Shimizu ................. C07C 51/44 |

FOREIGN PATENT DOCUMENTS

| | | | |
|---|---|---|---|
| EP | 3392233 | A1 | 10/2018 |
| EP | 3398930 | A1 | 11/2018 |
| JP | 62-251801 | A | 11/1987 |
| JP | 3-26301 | A | 2/1991 |
| JP | 9-120315 | A | 5/1997 |
| JP | 2017-165693 | A | 9/2017 |
| RU | 2102379 | C1 | 1/1998 |
| RU | 2282614 | C2 | 8/2006 |
| WO | 2012/081417 | A1 | 6/2012 |
| WO | 2017/057085 | A1 | 4/2017 |

OTHER PUBLICATIONS

Notification Concerning Transmittal of International Preliminary Report on Patentability (Forms PCT/IB/326) issued in counterpart International Application No. PCT/JP2020/033411 mailed Mar. 17, 2022, with Forms PCT/IB/373, PCT/IB/338 and PCT/ISA/237. (14 pages).

Office Action dated Oct. 27, 2022, issued in counterpart RU Application No. 2022108865/04 (018429). (10 pages).

European Patent Office, European Search Report dated Sep. 13, 2023 for European Application No. 208608919 filed Sep. 3, 2020, 6 pages.

* cited by examiner

ACETIC ACID MANUFACTURING METHOD

TECHNICAL FIELD

The present invention relates to a method of manufacturing acetic acid by carbonylating methanol. The present invention particularly relates to a method of stably operating a distillation column in a distillation step of finally separating product acetic acid from a reaction product containing acetic acid.

BACKGROUND ART

The method of manufacturing acetic acid by reacting methanol and carbon monoxide (CO) in the presence of a rhodium catalyst has been well known as so-called "Monsanto process". This method was originally developed as one employing a homogeneous catalytic reaction (PTL 1) in which methanol and carbon monoxide are reacted with each other in a reaction liquid obtained by dissolving a rhodium compound as a catalytic metal and an iodine compound, such as methyl iodide, as a promotor (reaction accelerator) in an acetic acid solvent containing water. Later, as a modification of the method, a method employing a heterogeneous catalytic reaction using a solid catalyst supporting a rhodium compound (PTL 2) was developed. Regardless of whether the catalytic reaction is homogeneous or heterogeneous, a liquid reaction product taken cut of a reactor, which is at high temperature and pressure, contains methanol, dissolved CO, methyl iodide, methyl acetate, dimethyl ether, acetic anhydride, water, etc., as well as acetic acid. Thus, in order to obtain product acetic acid, a purification step for removing the components other than acetic acid from the reaction product is necessary.

Such a purification step is carried out by, for example, a series of apparatuses (PTL 3) including a flasher, a light ends column, a drying (dehydration) column, and a heavy ends column. Firstly, the liquid reaction product from the reactor, which is at high temperature and pressure, is sprayed into the flasher vessel lower in pressure than the reactor, so that a part thereof vaporizes. The vapor (including acetic acid) obtained by the vaporization is introduced into the light ends column (upstream distillation column), whereas the liquid drawn out from the bottom of the flasher vessel is recycled to the reactor. At the light ends column, components whose boiling points are lower than that of acetic acid (boiling point=118.1° C.) by 50 degrees or more, such as CO, dimethyl ether, methyl iodide, methyl acetate, and methanol, are mainly drawn out as an overhead stream and recycled to the reactor. On the other hand, a liquid consisting of acetic acid and water is mainly drawn out from an intermediate portion or lower portion of the light ends column and introduced into the drying column (intermediate distillation column). Heavy components, such as acetic anhydride, are drawn out from the column bottom along with a part of acetic acid and recycled to the reactor. At the drying column, water is mainly drawn out as an overhead stream along with a part of the acetic acid whereas the acetic acid containing a small amount of impurities (crude acetic acid) is drawn out from a lower portion or the column bottom. The crude acetic acid thus drawn out is introduced into the heavy ends column (downstream distillation column), at which product acetic acid is drawn out as an overhead stream whereas impurities such as the heavy components are drawn out from the column bottom along with a part of the acetic acid.

Note that, among the above series of apparatuses, the drying column can be omitted by not providing the drying column as a separate column from the light ends column, drawing out the low-boiling point components and water together from the column top of the light ends column, and drawing out the crude acetic acid directly from a lower portion or the column bottom of the light ends column. Here, if hydrogen iodide produced by a reaction between methyl iodide and water is concentrated in the heavy ends column, it may cause corrosion of the apparatus. Thus, an aqueous solution of an alkaline agent, such as potassium hydroxide, is sometimes added in a stage before the heavy ends column or in the column for the purpose of preventing the corrosion (PTL 4).

CITATION LIST

Patent Literatures

PTL 1: Japanese Examined Patent Application Laid-Open No. S47-3334
PTL 2: Japanese Patent Application Laid-Open No. S63-253047
PTL 3: Japanese Patent Application Laid-Open No. 2014-131977
PTL 4: Japanese Patent No. 6007108 (internationally published on Jun. 23, 2012)

SUMMARY OF INVENTION

Technical Problem

As disclosed in PTL 3, in conventional practices, the product acetic acid is drawn out from the column top of the heavy ends column. However, a problem with such a configuration is that, when the crude acetic acid contains a certain amount of water, it cannot be drawn out from the column top to adjust the water content of the product acetic acid. In particular, when the amount of inflow of water into the heavy ends column increases due to a change in operation in an upstream process or the like or when an aqueous alkaline agent (such as an aqueous solution of an alkali metal hydroxide) is added in a stage before the heavy ends column or in the column in order to prevent corrosion of the apparatus due to concentration of hydrogen iodide inside the heavy ends column, the water content of the product acetic acid rises. This may deteriorate the quality.

In view of the above problem, an object of the present invention is to provide a method capable of removing water contained in crude acetic acid inside a heavy ends column.

Solution to Problem

The present invention solves the above problem by providing a method of manufacturing acetic acid by carbonylating a raw material consisting of one or more compounds selected from methanol, dimethyl ether, and methyl acetate with carbon monoxide, the method comprising: a reaction step of reacting the raw material with carbon monoxide in the presence of a catalyst inside a reactor to thereby form a reaction product containing acetic acid; and a purification step of purifying the reaction product obtained in the reaction step to thereby obtain product acetic acid, wherein the purification step includes a flash evaporation step of introducing the reaction product into a flasher vessel and vaporizing a part thereof to thereby separate the reaction product into a vapor-phase mixture containing acetic acid and low-boiling point components lower in boiling point than acetic acid, and a liquid-phase mixture containing acetic acid and a high-boiling point component higher in boiling point than acetic acid, a first distillation step of introducing the vapor-phase mixture into a light ends column consistig of at least one column and distilling the vapor-phase mixture to thereby separate and remove at least a part of the low-boiling point components from the vapor-phase mixture and obtain crude acetic acid, and a second distillation step of introducing the crude acetic acid into a heavy ends column and distilling the crude acetic acid to thereby further purify the crude acetic acid and obtain product acetic acid, and in the second distillation step, the low-boiling point components remaining in the crude acetic acid are drawn out from a column top of the heavy ends column, the product acetic acid is drawn out from an intermediate drawing stage of the heavy ends column, and a bottoms liquid surface level in the heavy ends column is controlled by adjusting an amount to be drawn out from the intermediate drawing stage.

DESCRIPTION OF EMBODIMENTS

Figure 1:
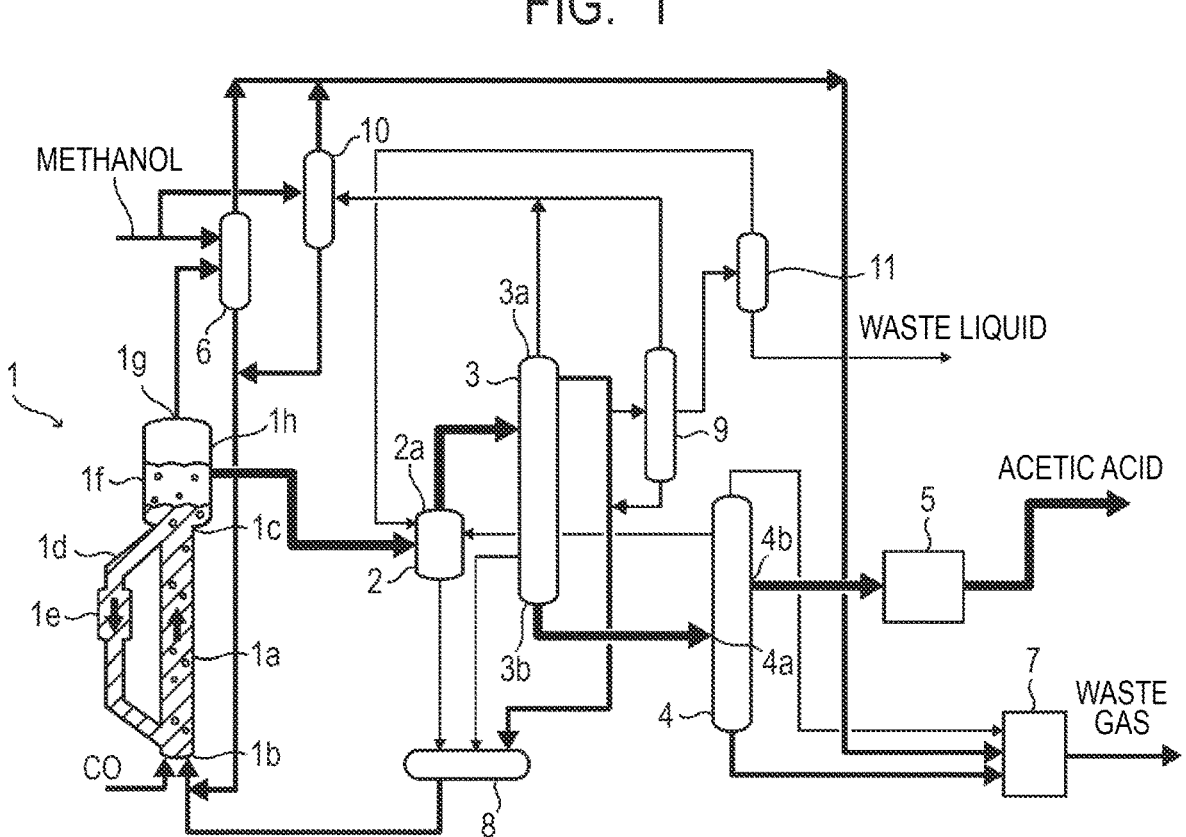
FIG. 1 illustrates one example of a flow of a process in an apparatus preferable for carrying out a method of the present invention.

The present invention relates to a method of manufacturing acetic acid by carbonylating a raw material consisting of one or more compounds selected from methanol, dimethyl ether, and methyl acetate with carbon monoxide (CO). By carbonylating methanol with CO the presence of a catalyst of a suitable metal (such as rhodium or iridium), acetic acid is mainly produced. Similarly, by carbonylating dimethyl ether with CO, methyl acetate is mainly produced and, by carbonylating methyl acetate with CO, acetic anhydride is mainly produced. Meanwhile, since these main products can be mutually transformed by further carbonylation, decarbonylation, hydrolysis, dehydration condensation, or the like, a liquid in a reactor (a reaction product containing acetic acid) is normally present as a mixture of these substances. Thus, reaction product containing acetic acid can be similarly obtained by using dimethyl ether or methyl acetate as the raw material in place of methanol (or along with methanol). Note that, as mentioned above, the metallic catalyst in the reactor may be dissolved as a metallic salt in a liquid phase (a liquid in the reactor) or present as a metal supported on a particulate support (made of a resin or the like) floated and suspended in the liquid phase.

Also, these substances are reaction products and, at the same time, function as reaction solvents. Thus, a raw material to be newly added can be reacted with CO in a reaction solvent containing any of these substances. Specifically, the constitution of the liquid in the reactor in equilibrium varies depending on reaction conditions such as the constitution of the raw material to be introduced as well as its amount to be introduced, temperature, and pressure, and the constitution of the catalyst. By drawing out such a liquid composition from the reactor (as a reaction product) and then purifying it by distillation or the like, a desired product compound (acetic acid in the present invention) is obtained. For this reason, the method of the present invention naturally includes: a reaction step of reacting a raw material with carbon monoxide (CO) in the presence of a catalyst inside a reactor to thereby form a reaction product containing acetic acid; and a purification step of purifying the reaction product produced in the reaction step to thereby obtain product acetic acid. Note that components other than the desired product compound separated in the purification step are usually recycled to the reactor or the like or disposed of.

In the method of the present invention, the purification step includes: a flash evaporation step of flash-evaporating the reaction product taken out of the reactor; a first distillation step of distillatively separating a mixture (vapor-phase mixture) separated to a vapor-phase side, by the vaporization in the flash evaporation step in an upstream distillation column (consisting of at least one column) called a light ends column, to thereby obtain an acetic acid product before final purification (crude acetic acid); and a second distillation step of performing the final purification on the crude acetic acid obtained in the first distillation step to thereby remove residual impurities such as a small amount of water and heavy components in a downstream distillation column called a heavy ends column. In the flash evaporation step, the reaction product is introduced (sprayed) into a flasher vessel, and a part of the reaction product is vaporized by a drop in ambient pressure. As a result, the reaction product is separated into a vapor-phase mixture containing acetic acid and low-boiling point components lower in boiling point than acetic acid, and a liquid-phase mixture containing acetic acid and high-boiling point components higher in boiling point than acetic acid. In the first distillation step, the vapor-phase mixture obtained by the separation in the flash evaporation step is introduced into the light ends column, and at least a part of the low-boiling point components is separated and removed as an overhead stream by a distillation operation. As a result, crude acetic acid being the vapor-phase mixture from which (at least a part of) the low-boiling point components have been removed is obtained (from a lower portion or the column bottom). In the second distillation step, the crude acetic acid obtained in the first distillation step is introduced into the heavy ends column and further purified by distillation. As a result, product acetic acid is obtained.

The crude acetic acid introduced in the heavy ends column consists originally of the components in the reaction product taken out of the reactor which are separated to the vapor-phase side in the flash evaporation step and from which water and the low-boiling point components are then further removed in the first distillation step. The crude acetic acid is therefore acetic acid hardly containing any components other than a small amount of residual water left unremoved in the previous step and the heavy (high-boiling point) components. Conventional heavy ends columns are aimed at removing heavy components from such a crude acetic acid product and does basically not take water removal into consideration. Hence, the product acetic acid is drawn out as an overhead stream. In contrast, in the present invention, in view of the fact that water, if not removed, may lower the quality of the product acetic acid, the configuration is such that the product acetic acid is drawn out as a side stream from an intermediate drawing stage of the heavy ends column and (the acetic acid containing) water is drawn out from the column top.

As mentioned earlier, in the manufacture of acetic acid by the methanol carbonylation method, in particular when methyl iodide is user as a promotor, the crude acetic acid contains hydrogen iodide produced by reaction of the methyl iodide with water, which may be concentrated in the heavy ends column and cause, corrosion of the apparatus. Then, to reduce this problem, one may add an aqueous solution of an alkaline agent, such as potassium hydroxide, into the upstream side of the heavy ends column (into the crude acetic acid). This raises the water content of the crude acid flowing into the heavy ends column, which in turn raises the water content of the product acetic acid as well. Considering the above, it is desirable to remove water from the column top of the heavy ends column. However, in the case of a conventional heavy ends column, the product acetic acid is drawn out from its column top, and it is therefore impossible to reduce the water content of the product acetic acid by drawing out water from the column top. In the method of the present invention, on the other hand, the product acetic acid is drawn out from the intermediate drawing stage. Thus, the water content of the product acetic acid can be adjusted by adjusting the amount to be drawn out from the column top.

Meanwhile, at acetic acid manufacturing plants, the amount of product acetic acid to be produced is usually adjusted according to the demand. The amount of product acetic acid to be produced is usually adjusted by adjusting the amounts of the raw material (methanol) and CO to be supplied and also adjusting the amount of product acetic acid to be drawn out of the heavy ends column. At this time, care needs to be taken to avoid a large change in the bottoms liquid surface level in the heavy ends column. This is because, if the sum of the amount of liquid down flow inside the column and the amount of the liquid (crude acetic acid) supplied from a dehydration column (or the light ends column) falls below the amount of vaporization by a reboiler and the bottoms liquid surface in the heavy ends column drops, distillation failure may occur and deteriorate the quality of the product acetic acid. In other words, controlling the bottoms liquid surface level in the heavy ends column at a constant level is essential for continuous and stable manufacture of acetic acid.

In order to control the bottoms liquid surface level at a constant level, the bottoms liquid surface level may be monitored and, if it changes, the amount of vaporization by the reboiler at the column bottom may be increased or decreased to adjust the bottoms liquid surface level so as to suppress its change. This is a common method performed in the case of adjusting the amount of acetic acid to be produced by adjusting the amount of its raw material to be supplied. If the amount of the raw material to be supplied changes, the amount of inflow of the crude acetic acid into the heavy ends column will change accordingly. Thus, if the amount of liquid down flow inside the column does not change, the bottoms liquid surface level will change too. At this time, the change in the bottoms liquid surface level may be suppressed by increasing or decreasing the amount of vaporization by the reboiler so as to cancel out the change. However, increasing or decreasing the amount of vaporization by the reboiler also increases or decreases the liquid holdup at the separation region in the heavy ends column, which accordingly increases or decreases the amount of liquid down flow in the column as well. For this reason, even when the amount of vaporization by the reboiler is increased or decreased, it will end up failing to maintain the bottoms liquid surface level constant unless the amount of the product acetic acid to be drawn cut is increased or decreased accordingly to adjust the amount of liquid down flow to the column bottom. In this respect, in the case of drawing cut the product acetic acid from the column top, as has been done conventionally, the liquid holdup in the column (vertical liquid amount distribution profile) can be maintained by increasing or decreasing the amount of vaporization by the reboiler and the amount of the product acetic acid to be drawn out in parallel with each other at substantially the same time. Hence, the bottoms liquid surface level can be maintained constant relatively easily.

However, in the case of employing the configuration in which the product acetic acid is drawn out as a side stream from the intermediate drawing stage of the heavy ends column, when the amount of vaporization by the reboiler is increased (or decreased), there will be a certain time difference (time lag) corresponding to the liquid volume (liquid residence time) from the column top to the intermediate drawing stage before the liquid surface level at the intermediate drawing stage (the amount of liquid down flow at this position) rises or (drops). That is, changing the amount of vaporization by the reboiler does not immediately change the liquid surface level at the intermediate drawing stage. Thus, the adjustment of the amount of the product acetic acid to be drawn out needs to be performed with a certain time difference with the adjustment of the amount of vaporization by the reboiler. Also, changing the amount of vaporization by the reboiler in a stepwise manner does not always change the liquid surface level at the intermediate drawing stage in a stepwise manner. It is therefore important to adjust the amount of the product acetic acid to be drawn out by taking into account the response characteristics of the liquid surface level at the intermediate drawing stage to a change in the amount of vaporization by the reboiler, and necessary to detect a change in the bottoms liquid surface level and adjust the amount of vaporization by the reboiler and the amount of the product acetic acid to be drawn out together so as to suppress that change.

One easy way to perform the above adjustment is to adjust the amount of vaporization by the reboiler based on the change in the bottoms liquid surface level and adjust the amount of the product acetic acid to be drawn out based on the change in the liquid surface level at the intermediate drawing stage. As mentioned above, in the present invention, if the responsiveness of the liquid surface level at the intermediate drawing stage to a change in the amount of vaporization by the reboiler is poor (deformation of the change profile in addition to the time difference), this poor responsiveness needs to be taken into account in order to adjust the amount of the product acetic acid to be drawn out based on a change in the bottoms liquid surface level. At this time, the adjustment of the amount of the product acetic acid to be drawn out may be performed based on the change in the liquid surface level at the intermediate drawing stage separately from the adjustment of the amount of vaporization by the reboiler. In this way, the bottoms liquid surface level can be controlled more easily.

FIG. 1 illustrates one example of a flow of a process in an entire apparatus preferable for carrying out the method of the present invention. In FIG. 1, a reactor 1 is a heterogeneous catalytic reaction apparatus for performing a reaction which manufactures acetic acid by carbonylating methanol with carbon monoxide (CO) in the presence of a rhodium catalyst. A vertical column 1a of the reactor 1 is filled with a particulate support (catalyst particles) supporting the rhodium catalyst. A liquid reaction medium containing acetic acid and/or methyl acetate as its main component is introduced from a bottom 1b and rises inside the vertical column 1a, so that a liquid fluidized bed is formed inside, the vertical column. The catalyst particles forming the liquid fluidized bed slowly rise inside the vertical column 1a with the upward stream of the liquid reaction medium and thereafter are separated from the upward liquid stream at a neck 1c, enter a catalyst circulation channel 1d, and slowly sink inside the catalyst circulation channel. A cooler 1e is provided at an intermediate portion of the catalyst circulation channel 1d, so that the catalyst particles are cooled while sinking inside the catalyst circulation channel and then return to the bottom 1b. Methanol and CO, which are raw materials to be reacted, are also introduced into the reactor 1 from the reactor bottom 1b. The methanol rises inside the vertical column 1a integrally with the liquid reaction medium, while the CO rises in the form of fine bubbles inside the vertical column 1a. The methanol and the CO bubbles in the liquid reaction medium rise inside the vertical column 1a while reacting with each other in the presence of the catalyst particles to thereby produce acetic acid, and are separated from the catalyst particles at the neck 1c. Thereafter, the liquid reaction medium containing the CO bubbles further rises inside the reactor 1. A gas containing the unreacted CO is separated at a liquid surface, formed inside a larger diameter part 1f of the reactor 1 and discharged to the outside of the reactor from a gas outlet 1g at the top. The liquid reaction medium after the gas separation is drawn out of the reactor from a liquid outlet 1h provided on the side of the larger diameter part 1f.

The liquid reaction medium drawn out of the reactor from the liquid outlet is sprayed into a flasher vessel 2. The pressure inside the flasher vessel 2 is maintained to be lower than the pressure inside the reactor 1, so that a part of the liquid reaction medium sprayed into the flasher vessel 2 vaporizes and becomes a vapor-phase mixture mainly containing vapors of acetic acid and low-boiling point components (components lower in boiling point than acetic acid, inclusive of water). The vapor-phase mixture formed inside the flasher vessel 2 is drawn out from its top 2a and introduced into a light ends column (here also serving as a dehydration column) 3. Inside the light ends column 3, the introduced vapor-phase mixture undergoes distillative separation. The low-boiling point components, such as methyl iodide, methyl acetate, methanol, and water, and a part of the acetic acid are drawn out from a column top 3a, whereas a liquid containing the acetic acid as its main component (crude acetic acid) is drawn out from a column bottom 3b and introduced into a heavy ends column (finishing column) 4 from its crude acetic acid inlet 4a. Inside the heavy ends column 4, finishing distillative separation is performed. The resultant product acetic acid is drawn out as a side stream from a product acetic acid outlet 4b located at a position (intermediate drawing stage) somewhat higher than the crude acetic acid inlet 4a. The product acetic acid drawn out is temporarily stored in a product conditioning tank 5 to undergo final conditioning, and then taken out as product acetic acid.

Figure 2:
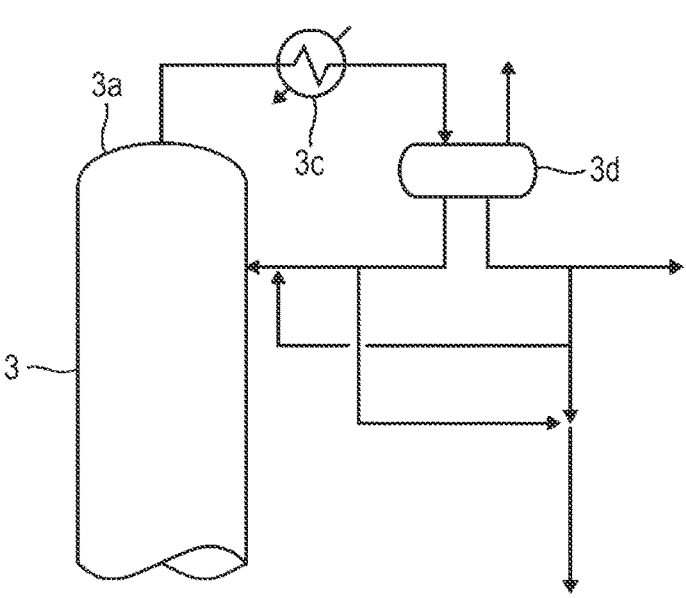
FIG. 2 illustrates a detailed flow at an upper part of a light ends column (dehydration column) in the apparatus in FIG. 1.

The gas containing the unreacted CO that has been discharged from the gas outlet 1g of the reactor 1 comes into contact with a stream (shower) of raw material methanol in a high-pressure absorption column 6, so that the CO is collected. The gas is then incinerated in an incinerator 7. The raw material methanol having contacted the CO-containing gas and absorbed its CO in the high-pressure absorption column 6 is guided from its column bottom to the bottom 1b of the reactor 1 to be introduced into the reactor 1. Also, as illustrated in FIG. 2, the low-boiling point components and the part of the acetic acid drawn out from the column top 3a of the light ends column 3 are partly liquefied in a condenser 3c. The liquefied components are separated in a gas-liquid separator 3d, so that one part is returned to the light ends column, one part is recycled to the reactor 1 via a liquid collection tank 8, and one part undergoes gas-liquid separation again in an excess water column 9. On the other hand, the components separated into a gas phase in the gas-liquid separator 3d mainly contain the low-boiling point components other than water, and are therefore brought into contact with a stream (shower) of raw material methanol in a low-pressure absorption column 10, so that the low-boiling point components are collected. The gas phase is then incinerated in the incinerator 7. Moreover, a liquid component drawn out from the bottom of the excess water column 9 is recycled to the reactor 1 via the liquid collection tank 8. A liquid component drawn out from an intermediate portion of the excess water column 9 is sent to an ethyl iodide collection column 11, in which ethyl iodide is collected, and then sent to a waster liquid treatment apparatus. Also, the liquid accumulated at the bottom of the flasher vessel 2 is also recycled to the reactor 1 via the liquid collection tank 8. Note that, from the bottom of the heavy ends column 4, a liquid containing a small amount of heavy (high-boiling point) components separated as impurities from the crude acetic acid is drawn out. This is incinerated in the incinerator 7.

Figure 3:
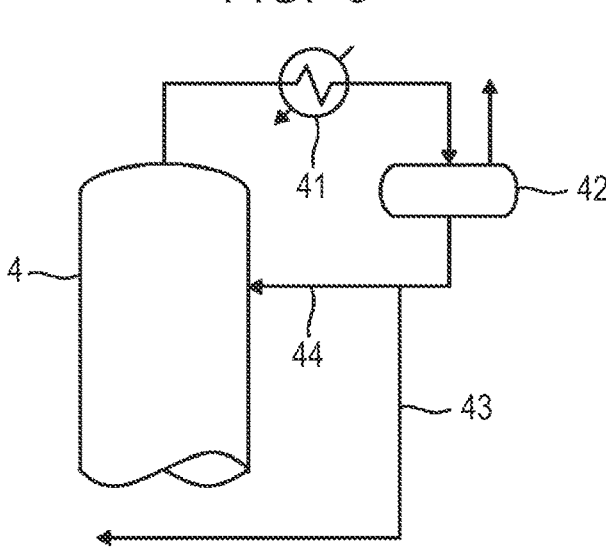
FIG. 3 illustrates a detailed flow at an upper part of a heavy ends column (finishing column) in the apparatus in FIG. 1.

As mentioned above, the heavy ends column 4 is a distillation column for performing final purification, i.e., finishing distillative separation, of the crude acetic acid product. This distillation column does not need to be exclusively special and only needs to be a plate column or a packed column of a common type including, at the column bottom, a reboiler that vaporizes a liquid accumulated and, at the column top, a condenser 41 that condenses a vapor drawn out and a gas-liquid separator 42, as illustrated in FIG. 3. The depth of the liquid accumulated in the liquid pool at the column bottom of the heavy ends column 4 (bottoms liquid surface level) changes according to the balance between the amount of vaporization by the heating by the reboiler (the amount of vaporization by the reboiler) and the amount of liquid down flow from an upper portion of the inside of the column (including the crude acetic acid introduced into the column from the light ends column 3). In a steady state, both amounts are balanced, and the bottoms liquid surface level is therefore maintained constant. However, if the bottoms liquid surface level changes (in particular, if the level drops abruptly), the reboiler may be in a heating state with no liquid in it. In this case, no vapor will rise, which leads to a failure to perform a distillation operation. In many cases, the bottoms liquid surface level is changed particularly by a change in the amount of liquid down flow in the column, and there are two main causes of the change in the amount of liquid down flow. One is a change in the amount of the liquid returned to the column top from the gas-liquid separator 42. The other is a change in the amount of the crude acetic acid product supplied and introduced from the crude acetic acid inlet 4a.

As mentioned earlier, in conventional practices, a part of the liquid obtained by condensing the vapor drawn out from the column top of the heavy ends column with the condenser 41 and separating the resultant product with the gas-liquid separator 42 is drawn out as product acetic acid. This is because the crude acetic acid to be introduced into the column from the crude acetic acid inlet 4*a* has an acetic acid content of 98% or more and usually it hardly contains low-boiling point components (contains a certain amount of water), and therefore the necessity to separate low-boiling point components from the column top is low. However, since the high-boiling point components (in particular alkali metal salts such as sodium iodide and sodium acetate produced when an aqueous solution of an alkaline agent is added, in addition to propionic acid and the like contained in small amounts) affect the product quality even when the amount is small, they are drawn out from the column bottom of the heavy ends column and separated and removed. Note that the amount to be drawn out from the column bottom of the heavy ends column 4 is about $\frac{1}{1000}$ of the amount of inflow from the crude acetic acid inlet 4*a*, and adjusting this amount will hardly affect the bottoms liquid surface level.

In contrast, in the present invention, the liquid drawn out from the drawing port (intermediate drawing stage) 4*b* at an intermediate portion of the heavy ends column is handled as product acetic acid, and the water content of the product acetic acid is controlled by adjusting the amount of the vapor to be drawn out from the column top. Moreover, to maintain the bottoms liquid surface level constant, it is preferable to adjust the amount of the product acetic acid to be drawn out based on the liquid surface level at this intermediate drawing stage, as mentioned earlier. Here, in the case of a plate column, the liquid surface level at the intermediate drawing stage may be defined as the liquid depth on a plate corresponding to the drawing stage. In the case of a packed column, however, the liquid surface level at the intermediate drawing stage cannot be defined in such a manner. For this reason, a measure that reflects the liquid amount (the amount of liquid down flow) at the intermediate drawing stage may be set, such as the amount of flow of the liquid flowing through a tube connected to a liquid collector buried in the packed layer, and that may be defined as the liquid surface level at the intermediate drawing stage. With such a definition, the measure of the liquid surface level at the intermediate drawing stage serves as a general idea that can be applied not only to a plate column but also to a packed column.

EXAMPLES

Example 1

Figure 4:
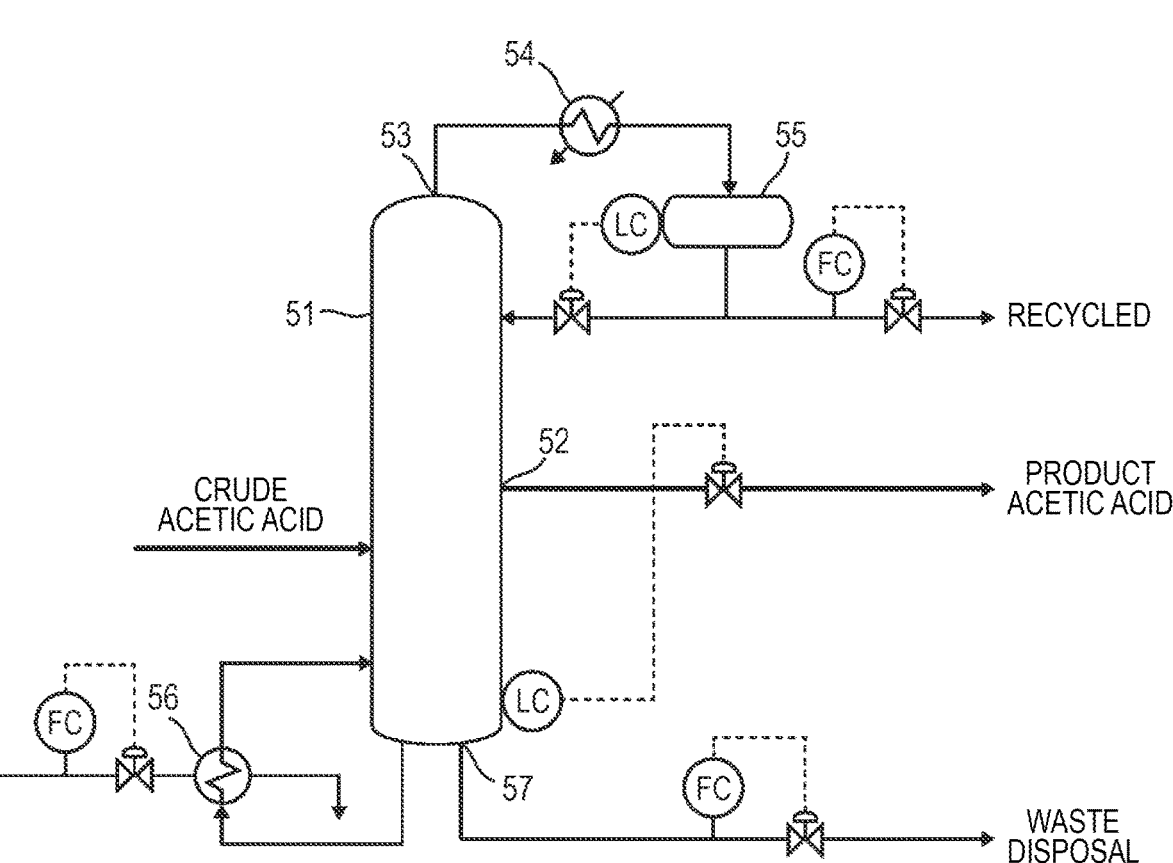
FIG. 4 illustrates a flow around a heavy ends column in Example 1 and how it is controlled.

FIG. 4 illustrates a configuration example in which product acetic acid is drawn out as a side stream from a drawing port (intermediate drawing port) 52 at an intermediate height (intermediate drawing stage) of a heavy ends column 51, a vapor drawn out from a drawing port (column top drawing port) 53 provided at the column top is condensed in a condenser 54 and received in a condensate reception tank 55, and a part of an outflow liquid taken out of the condensate reception tank is discharged to the outside of the column and recycled to the reactor not illustrated as needed whereas the remaining part of the outflow liquid is returned to an upper portion of the column. Crude acetic acid drawn out of the light ends column (or dehydration column) not illustrated is introduced into a lower portion of the column, and the liquid accumulated in the liquid pool at the column bottom is heated by a reboiler 56 into a vapor, which rises inside the column to the column top while coming into countercurrent contact with a liquid flowing down inside the column to thereby exchange heat (and substances) with it. Note that a liquid containing heavy components is drawn out from a drawing port (column bottom drawing port) 57 at the column bottom and is recycled to the reactor or disposed of.

The intermediate drawing port 52, through which to draw out the product acetic acid, is configured such that, in the case of a plate column, the liquid at an intermediate drawing stage (a plate between the uppermost stage and the lowermost stage) is drawn out and, in the case of a packed column, the liquid is drawn out from a liquid collection device provided below the upper surface of the packed layer and above its lower surface. Herein, for the plate column and the packed column, the position at the above intermediate height at which to drawn out the product acetic acid will be referred to in common as the intermediate drawing stage.

In the present example, if the liquid surface height of the liquid accumulated in the liquid pool at the column bottom (bottoms liquid surface level) changes due to a change in the amount supplied to the heavy ends column, the amount of the product acetic acid to be drawn out from the intermediate drawing port 52 is adjusted based on that change so as to bring the bottoms liquid surface level back to the original position. This adjustment of the amount of the product acetic acid to be drawn out is not limited to a particular method. The adjustment may be performed by feedback control, such as PID control. Alternatively, an automatic control method may be used which utilizes the response characteristics (of the amount of inflow of the crude acetic acid to a change the amount of the raw material to be introduced) of the system consisting of a series of apparatuses from the reactor to the heavy ends column.

Changing the amount of the product acetic acid to be drawn cut changes the amount of liquid down flow at the region below the intermediate drawing stage, but it does not have an immediate impact on the bottoms liquid surface level since a certain residence time is necessary for the liquid to fall from the intermediate drawing stage to the column bottom. However, once a predetermined time passes, the effect of the change in the amount of the product acetic acid to be drawn out starts to appear on the bottoms liquid surface level. Thus, by adjusting (changing) the amount of the product acetic acid to be drawn out, it is possible to bring the bottoms liquid surface level back to the original position while maintaining the amount of vaporization by the reboiler, although a certain time is required before the bottoms liquid surface level stabilizes.

For example, assuming that the amount of inflow of the crude acetic acid into the heavy ends column 51 is 100, the amount of the condensate obtained by the condensation of what is drawn out from the column top drawing port 53 and recycled to the reactor or disposed of may be 1, and the amount of the liquid drawn out from the column bottom drawing port 57 and disposed of may be 0.1. In this case, a steady state is maintained when the amount of the product acetic acid drawn out from the intermediate drawing port 52 is 98.9. Now, assume that the amount of inflow of the crude acetic acid has decreased from 100 to 98 for some reason, and the bottoms liquid surface level has started to drop due to that. Then, based on a signal from a liquid level gauge having detected the drop in the bottoms liquid surface level, the control system operates so as to decrease the amount of the product acetic acid to be drawn out from the intermediate drawing port 52. As a result, the amount of liquid down flow at the region below the intermediate drawing stage increases, so that the drop in the bottoms liquid surface level decreases and returns to the original level as a predetermined time passes. In the case of feedback control (PID control), the amount to be drawn out from the intermediate drawing port 52 is adjusted based on the displacement of the bottoms liquid surface level itself (factor of proportionality) as well as the integrated quantity of the displacement (integrating factor) and its change speed (differentiating factor). Here, with conventional passive control, it is expected to take a certain time before the bottoms liquid surface level converges due to the liquid residence time from the intermediate drawing stage to the column bottom. Thus, in order to hasten the convergence, it is preferable to perform active (feedforward) control that utilizes AI having a learning function. Either way, a new steady state is finally reached in a state where the amount of the product acetic acid to be drawn out from the intermediate drawing port 52 stabilizes at 96.9.

Example 2

In the present example, the structure around the heavy ends column is as illustrated in FIG. 4 and is similar to Example 1. The present example, however, assumes a case where the amount of water to be supplied to the heavy ends column (the content of water in the crude acetic acid) has increased due to a change in operation in an upstream process or the like. In this case, the amount of water in the heavy ends column increases, but the bottoms liquid surface level does not change and the amount of vaporization does not change either. On the other hand, in order to adjust the amount of water in the system, it is necessary to increase the amount to be drawn out from the column top (decrease the amount of the condensate to be returned to the upper portion of the column). Then, by accordingly decreasing the amount of the acetic acid to be drawn out from the intermediate stage, the amount of liquid down flow to the column bottom will consequently remain unchanged. This makes it possible to maintain the bottoms liquid surface level and also keep the water content of the product acetic acid from rising and thus maintain its quality.

Example 3

Figure 5A:
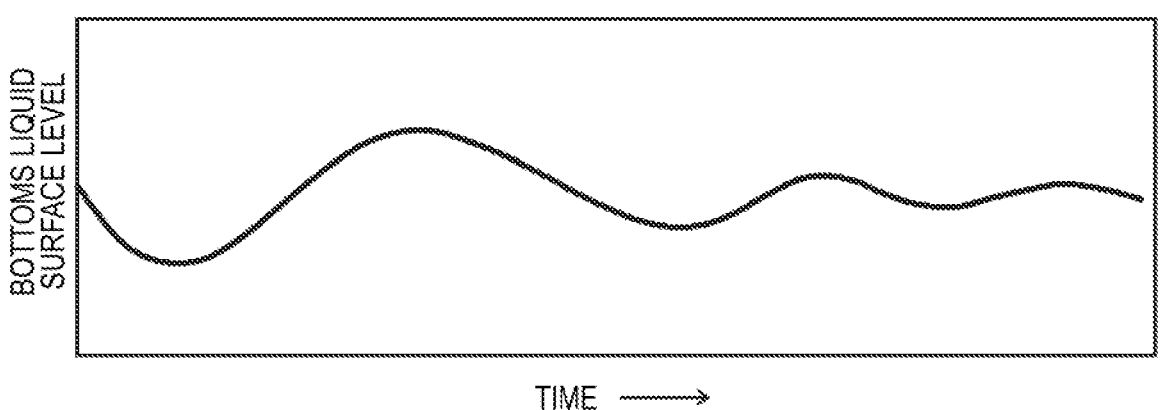
FIG. 5(a) and FIG. 5(b) schematically illustrate how the bottoms liquid surface level changes in Example 1 and Example 3.
Figure 5B:
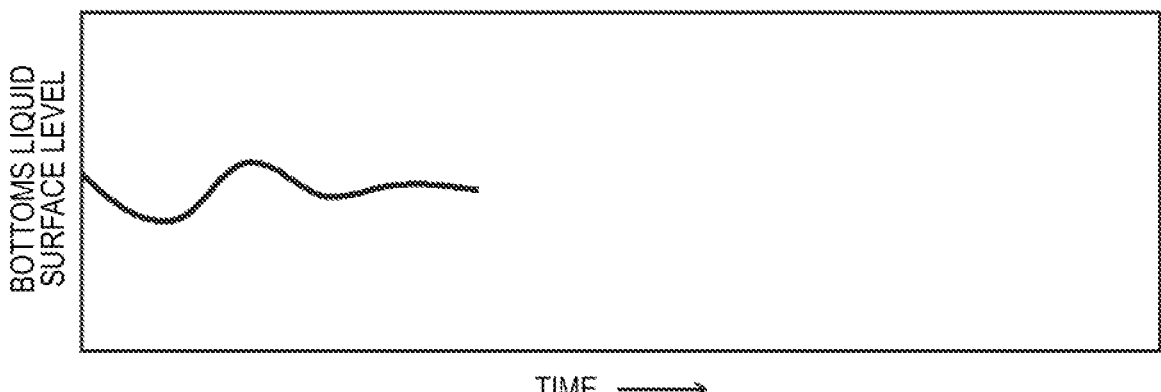

In Example 1 and Example 2, the bottoms liquid surface level is maintained constant by adjusting the amount of the product acetic acid to be drawn out from the intermediate drawing port while maintaining the amount of vaporization by the reboiler. However, as mentioned above, with conventional (passive) feedback control, it may take a substantial time before the bottoms liquid surface level converges due to the liquid residence time from the intermediate drawing port to the column bottom. For example, in Example 1, based on the drop in the bottoms liquid surface level due to a decrease in the amount of inflow of the crude acetic acid, the amount of the product acetic acid to be drawn out from the intermediate drawing port is decreased. However, it does not have an immediate impact on reducing the drop in the bottoms liquid surface level, so that the bottoms liquid surface level keeps dropping for a while. Moreover, if the amount to be drawn out from the intermediate portion is excessively decreased in response to that, the bottoms liquid surface level will reverse to rise after the elapse of a predetermined time. Furthermore, if the amount to be drawn out from the intermediate portion is excessively increased in response to that, the bottoms liquid surface level will drop again. If this is repeated, the bottoms liquid surface level will exhibit behavior in which it fluctuates greatly and then converge gradually, as illustrated in FIG. 5(*a*).

Thus, in the present example, in order to prevent behavior as mentioned above, which may occur in Example 1, the amount of vaporization by the reboiler is adjusted according to the bottoms liquid surface level and also the amount of the product acetic acid to be drawn out from the intermediate drawing port is adjusted. Specifically, in FIG. 4, the configuration is such that the amount of the product acetic acid to be drawn out from the intermediate drawing port is adjusted in accordance with a control signal from a controller LC monitoring the bottoms liquid surface level. However, this may be changed into a configuration in which the amount of flow of steam for heating the reboiler 56 is adjusted in accordance with the control signal from the controller LC monitoring the bottoms liquid surface level. This configuration improves the responsiveness of adjustment of the bottoms liquid surface level to a change in the amount of inflow of the crude acetic acid. Accordingly, as illustrated in FIG. 5(*b*), the range of fluctuation of the bottoms liquid surface level and the time taken to reach convergence are smaller and shorter than those in Example 1. Specifically, the time taken to reach convergence is shortened to about $\frac{1}{10}$ to $\frac{1}{500}$ of that in Example 1, though this depends on the configuration of the control system and the liquid residence time at the region below the intermediate drawing stage.

Note that, in the present example, the bottoms liquid surface level is controlled directly by adjusting the amount of vaporization by the reboiler. The change in the liquid holdup in the column resulting from the adjustment of the amount of vaporization by the reboiler is handled by adjusting the amount of the product acetic acid to be drawn out from the intermediate drawing port after the elapse of a predetermined time difference. Thus, as a whole, the bottoms liquid surface level is still controlled by adjusting the amount to be drawn out from the intermediate drawing port.

Example 4

As in Example 3, the present example involves controlling the bottoms liquid surface level by adjusting the amount of vaporization by the reboiler, but assumes a case where not only the amount of inflow of the crude acetic acid into the heavy ends column has increased but also the amount of water supplied has increased (the concentration of water in the crude acetic acid has also risen). In this case, the amount of vaporization may be increased according to the rise of the bottoms liquid surface in the heavy ends column. This increases the amount of the vapor to be drawn out from the column top drawing port 53, so that the liquid surface in the condensate reception tank 55 rises. Then, by increasing the amount of the condensate to be returned into the column according to the rise of the liquid surface in the condensate reception tank, the separation of water and acetic acid is facilitated.

Specifically, to remove water from the heavy ends column, it is effective to increase the amount of the vapor to be drawn out from the column top drawing port 53. However, in Example 2, the amount of vaporization by the reboiler is kept constant. Hence, the amount to be drawn out from the column top drawing port itself does not change, and only the amount of the condensate to be returned to the upper portion of the column changes (decreases) as the amount to be recycled to the reactor increases. In contrast, in the present example, the amount of vaporization by the reboiler is increased to thereby increase the amount of the vapor to be drawn out from the column top drawing port 53, and an amount of the condensate corresponding to that increase is returned into the column (which affects the distillative separation performance at the region above the intermediate drawing stage). This facilitates the separation of water and acetic acid. Thus, more water can be efficiently separated and removed from the column top than in Example 2.

Note that the above assumes the case where the amount of inflow of the crude acetic acid has increased with an increase in the water content of the crude acetic acid, and therefore the increase in the amount of vaporization by the reboiler and the increase in the amount to be returned are balanced. However, when the water content increases without an increase in the amount of inflow of the crude acetic acid, the efficiency of the water removal can be raised by increasing the amount of vaporization by the reboiler. In either case, the amount of the product acetic acid to be drawn out from the intermediate drawing port needs to be adjusted so order for the bottoms liquid surface level to be finally maintained. In other words, in the present example too, as a whole, the bottoms liquid surface level is controlled by adjusting the amount to be drawn out from the intermediate drawing port.

Example 5

Figure 6:
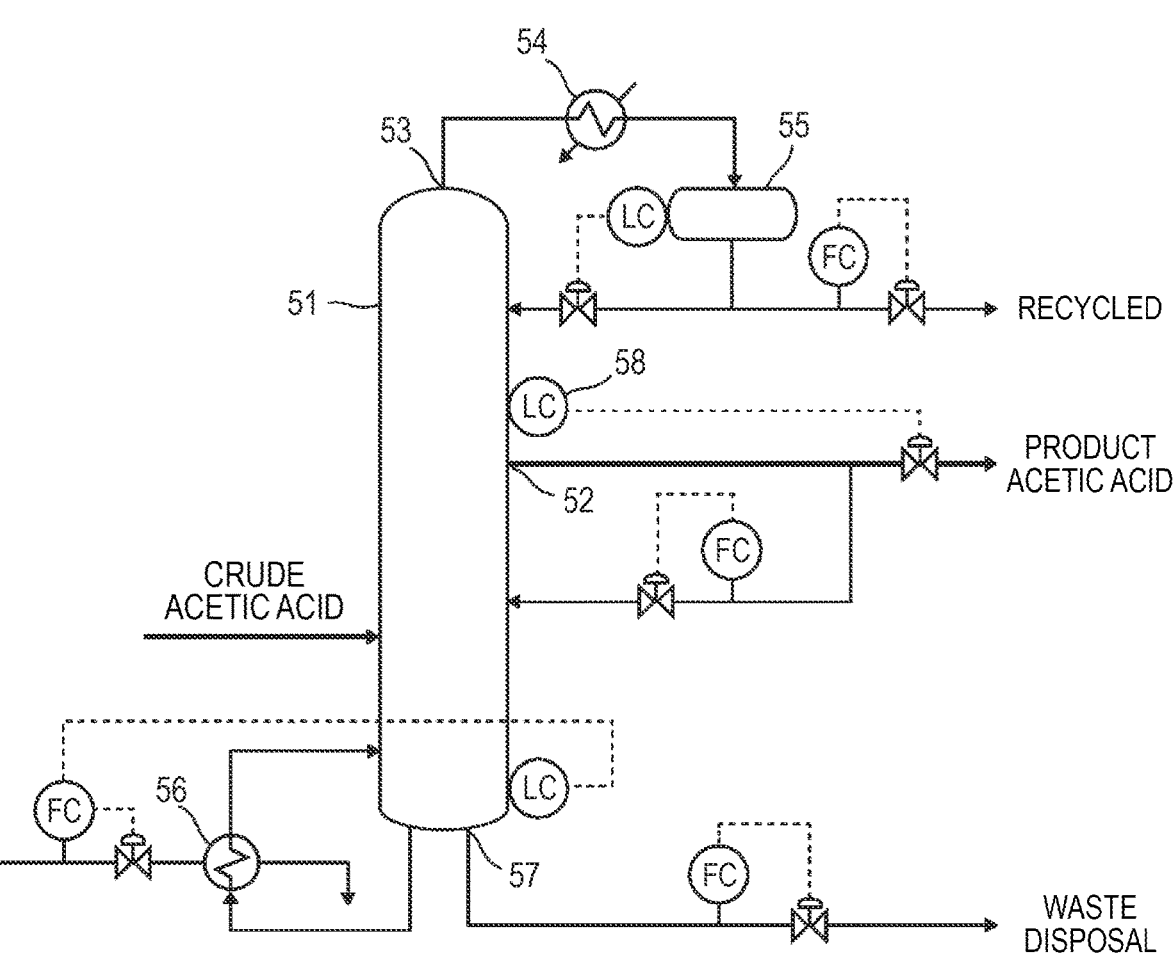
FIG. 6 illustrates a flow around a heavy ends column in Example 3 and how it is controlled.

In the present example, the configuration in Examples 3 and 4 is further modified. As illustrated in FIG. 6, as for the control of the bottoms liquid surface level itself, the bottoms liquid surface level is controlled to be kept constant by adjusting the amount of flow of steam for heating the reboiler 56 (i.e., the amount of vaporization by the reboiler) while monitoring the bottoms liquid surface level. Besides this, a liquid level gauge (liquid meter) 50 that monitors the liquid surface level at the intermediate drawing stage is provided and, when the limpid surface level (the amount of liquid down flow) at the intermediate drawing stage changes as a result of adjusting the amount of vaporization by the reboiler, the amount of the product acetic acid to be drawn out from the intermediate drawing port 52 is adjusted to increase or decrease accordingly. With this configuration, the timing for adjusting the amount of the product acetic acid to be drawn out from the intermediate drawing port can be controlled more accordingly. Accordingly, the range of fluctuation of the bottoms liquid surface level and the time taken to reach convergence can be even smaller and shorter than those in Example 3 and Example 4. Moreover, in the present example too, the bottoms liquid surface level is controlled directly by adjusting the amount of vaporization by the reboiler. Here, the change in the liquid surface level at the intermediate drawing stage that appears with a certain time lag due to the adjustment of the amount of vaporization by the reboiler is monitored, based on which the amount of the product acetic acid to be drawn out from the intermediate drawing port is increased or decreased. Thus, as a whole, the bottoms liquid surface level is controlled by adjusting the amount to be drawn out from the intermediate drawing port.

In the present example too, when the concentration of water in the crude acetic acid rises, the amount of vaporization by the reboiler is increased to increase the amount of the vapor to be drawn out from the column top drawing port 53, regardless of Whether the bottoms liquid surface level has changed or not. The amount of the condensate to be returned into the column (which affects the distillative separation performance at the region above the intermediate drawing stage) is increased by an amount corresponding to the above increase. This raises the efficiency of the separation of water and acetic acid. Thus, more water can be separated and removed from the column top. Here, if the amount of vaporization by the reboiler is suddenly increased without the amount of inflow of the crude acetic acid changed, the bottoms liquid surface level will drop. Thus, in such a case, the drop in the bottoms liquid surface level can be suppressed by following a procedure in which firstly a part of the product acetic acid drawn out from the intermediate drawing port 52 is returned to the column bottom (that is, substantially decreasing the amount to be drawn out from the intermediate drawing port) to thereby raise the bottoms liquid surface level; and thereafter the amount of vaporization by the reboiler is increased. The product acetic acid thus returned to the column bottom has been drawn out from the intermediate drawing port but ended up not being drawn out to the outside. Thus, in this case too, as a whole, the bottoms liquid surface level is controlled by adjusting the amount to be drawn out from the intermediate drawing port. Moreover, as mentioned above, the configuration can be such that the drop in the bottoms liquid surface level is minimized by performing control such that a part of the product acetic acid is returned to the column bottom prior to the increase in the amount of vaporization by the reboiler.

Comparative Example

Figure 7:
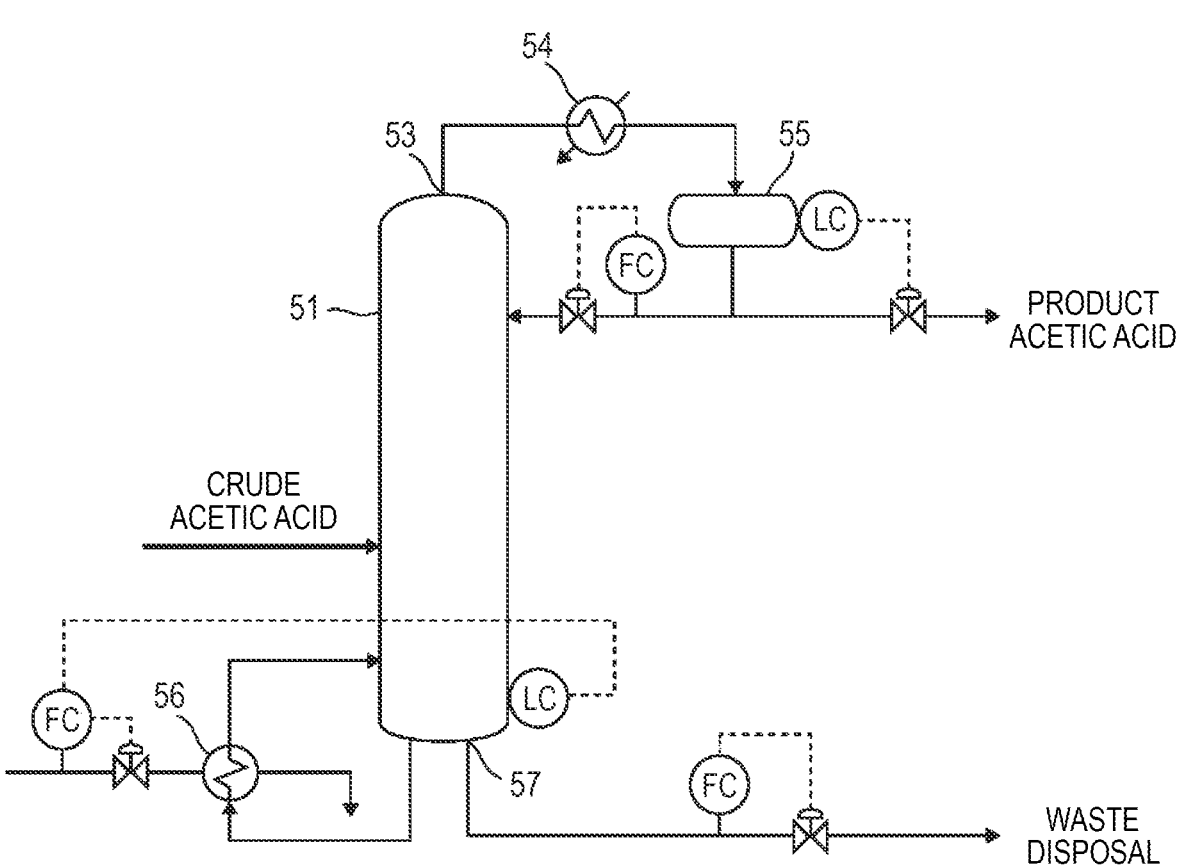
FIG. 7 illustrates a flow around a heavy ends column in a comparative example and how it is controlled.

In the present comparative example, as illustrated in FIG. 7, no intermediate drawing port is provided, and the product acetic acid is drawn out only from the column top drawing port 53. In the present example, since the product acetic acid is drawn out from the column top drawing port, the bottoms liquid surface level can be adjusted by adjusting the amount of the product acetic acid to be drawn out. However, if the amount of water contained in the crude acetic acid increases due to a change in an upstream operation, addition of an alkaline aqueous solution, or the like, the amount of water contained in the product acetic acid will be large since it is impossible to separate water from the product acetic acid. This may affect the product quality.

This application claims the benefit of priority from Japanese Patent Application No. 2019-161901, filed on Sep. 5, 2019, the contents of which are incorporated by reference as a part of this application.

REFERENCE SIGNS LIST

1 reactor
1*a* vertical column
1*b* bottom
1*c* neck
1*d* catalyst circulation channel
1*e* cooler
1*f* larger diameter part
1*g* gas outlet
1*h* liquid outlet
2 flasher vessel
2*a* top
3 light ends column
3*a* column top
3*b* column bottom
4 heavy ends column
4*a* crude acetic acid inlet
4*b* product acetic acid outlet
5 product conditioning tank
6 high-pressure absorption column
7 incinerator
8 liquid collection tank
9 excess water column
10 low-pressure absorption column
11 ethyl iodide collection column
41 condenser
42 gas-liquid separator 43 stream to be drawn out to outside
44 stream to be returned to column top
51 heavy ends column
52 intermediate drawing port
53 column top drawing port
54 condenser
55 condensate reception tank
56 reboiler
57 column bottom drawing port
58 liquid level gauge (liquid meter) at intermediate draw-ing stage

The invention claimed is:

1. A method of manufacturing acetic acid by carbonylating a raw material comprising one or more compounds selected from methanol, dimethyl ether, or methyl acetate with carbon monoxide, the method comprising: a reaction step of reacting the raw material with carbon monoxide in the presence of a catalyst inside a reactor to thereby form a reaction mixture containing acetic acid; and a purification step of purifying the reaction mixture formed in the reaction step to thereby obtain product acetic acid, wherein the purification step includes a flash evaporation step of introducing the reaction mixture into a flasher vessel and vaporizing a part thereof to thereby separate the reaction mixture into a vapor-phase mixture containing acetic acid and low-boiling point components lower in boiling point than acetic acid, and a liquid-phase mixture containing acetic acid and a high-boiling point component higher in boiling point than acetic acid, a first distillation step of introducing the vapor-phase mixture into a light ends column consisting of at least one column and distilling the vapor-phase mixture to thereby separate and remove at least a part of the low-boiling point components from the vapor-phase mixture and obtain crude acetic acid, and a second distillation step of introducing the crude acetic acid into a heavy ends column and distilling the crude acetic acid to thereby further purify the crude acetic acid and obtain product acetic acid, and in the second distillation step, the low-boiling point components remaining in the crude acetic acid are drawn out from a column top of the heavy ends column, the product acetic acid is drawn out from an intermediate drawing stage of the heavy ends column, and a bottoms liquid surface level in the heavy ends column is controlled by adjusting an amount to be drawn out from the intermediate drawing stage.

2. The method according to claim 1, wherein the low-boiling point components drawn out from the column top of the heavy ends column in the second distillation step include water.

3. The method according to claim 1, wherein an amount to be drawn out from the column top and the amount to be drawn out from the intermediate drawing stage are adjusted together.

4. The method according to claim 1, wherein an amount of vaporization by a reboiler at a column bottom and the amount to be drawn out from the intermediate drawing stage are adjusted based on a change in the bottoms liquid surface level.

5. The method according to claim 1, wherein an amount of vaporization by a reboiler at a column bottom is adjusted based on a change in the bottoms liquid surface level, and the amount to be drawn out from the intermediate drawing stage is adjusted based on a liquid surface level at the intermediate drawing stage.

6. The method according to claim 1, wherein the amount to be drawn out from the intermediate drawing stage is adjusted by returning a part of the product acetic acid drawn out from the intermediate drawing stage to a lower portion of the heavy ends column.

7. The method according to claim 1, wherein
in the reaction step, methyl iodide is present as a promotor inside the reactor, and
in the purification step, an aqueous alkaline agent is added in a stage before the heavy ends column or in the heavy ends column.

8. The method according to claim 7, wherein the aqueous alkaline agent is added to the crude acetic acid obtained in the first distillation step.

9. The method according to claim 1, wherein in the reaction step, the catalyst is dissolved as a metallic salt in a liquid phase.

10. The method according to claim 1, wherein in the reaction step, the catalyst is present as a metal supported on a particulate support.

* * * * *